United States Patent [19]

Lucarelli et al.

[11] Patent Number: 5,516,869
[45] Date of Patent: May 14, 1996

[54] AMINO ACID FUNCTIONALIZED SILICONES AND METHOD FOR PREPARATION

[75] Inventors: Michael A. Lucarelli, Ballston Spa; William J. Raleigh, Rensselaer, both of N.Y.

[73] Assignee: General Electric Company, Waterford, N.Y.

[21] Appl. No.: 370,596

[22] Filed: Jan. 10, 1995

Related U.S. Application Data

[62] Division of Ser. No. 146,357, Oct. 29, 1993, Pat. No. 5,399,653, which is a division of Ser. No. 934,051, Aug. 21, 1992, Pat. No. 5,272,241.

[51] Int. Cl.[6] .................. C08G 77/06; C08G 77/08
[52] U.S. Cl. .................. 528/15; 528/26; 528/28; 528/41; 528/38; 528/23; 556/418
[58] Field of Search ................. 528/15, 26, 28, 528/41, 38, 23; 556/418

[56] References Cited

U.S. PATENT DOCUMENTS

| | | | |
|---|---|---|---|
| 3,249,586 | 5/1966 | Haluska | 260/46.5 |
| 3,278,485 | 10/1966 | Morgan et al. | 260/46.5 |
| 3,716,569 | 2/1973 | Redmore et al. | 260/448.8 N |
| 4,248,825 | 2/1981 | Coon et al. | 264/213 |
| 4,488,864 | 12/1984 | Borrelli et al. | 430/13 |
| 4,785,067 | 11/1988 | Brumbill | 528/26 |
| 4,847,397 | 7/1989 | Sawaragi et al. | 556/418 |
| 4,912,240 | 3/1990 | Owen et al. | 556/418 |
| 4,946,818 | 8/1990 | Lewis | 502/158 |
| 5,028,485 | 7/1991 | van Hooijdonk | 428/355 |
| 5,115,049 | 5/1992 | Imperante et al. | 525/479 |
| 5,272,241 | 12/1993 | Lucarelli et al. | 528/15 |
| 5,399,653 | 3/1995 | Lucarelli et al. | 528/28 |

*Primary Examiner*—Margaret Glass

[57] ABSTRACT

Organofunctional siloxanes useful in a wide variety of personal care and plastics applications are disclosed having a carboxyalkylaminoalkyl functionality.

7 Claims, No Drawings

AMINO ACID FUNCTIONALIZED SILICONES AND METHOD FOR PREPARATION

This is a divisional of application Ser. No. 08/146,357, filed on Oct. 29, 1993, now U.S. Pat. No. 5,399,6653, which is a Divisional of 07/934,051, filed on Aug. 21, 1992, U.S. Pat. No. 5,272,241.

The present invention relates to silicones useful in both the personal care and plastics industries. More particularly, the present invention relates to an organofunctional silicone. Most particularly, the present invention relates to amino acid functionalized silicones.

BACKGROUND OF THE PRESENT INVENTION

Organofunctional silicones are well known in the art. The siloxane may be functionalized with substituents such as carboxy, amido, ketoxy, epoxy, vinyl, hydride, mercapto, amino, glycidoxy, methacryloxy and alkoxy groups. These organofunctionalities are generally employed to obtain specific physical and chemical properties. Aminoalkyl-substituted silicones, for example, increase water solubility and are used in automobile polishes to enhance durability and confer detergent resistance through bonding with paint films. Other functionalized fluids find use in applications such as textile lubricants, softeners and antistats. A variety of amino functional siloxanes are described in the prior art.

Brumbill, U.S. Pat. No. 4,785,067, teaches a protective coating consisting essentially of a polysiloxane copolymer prepared by the reaction of a trimethyl end blocked polyamine silicone fluid including amino alkyl groups with a saturated aliphatic carboxylic acid groups to produce a polysiloxane copolymer including alkyl amine groups.

Van Hooijdonk, U.S. Pat. No. 5,028,485, teaches a pressure sensitive adhesive composition suitable for skin contact comprising a silane compound having at least one amino functional group.

Imperante et al., U.S. Pat. No. 5,115,049, teach the preparation of fatty carboxylic acid salts of organofunctional silicone amines, where the amino pendant functionality is present within the polymer and which are produced by the neutralization of a silicone amine with a fatty carboxylic acid.

It has now been found that novel amino acid functionalized silicones can be produced, and that such compounds are useful in a variety of plastic and personal care applications.

SUMMARY OF THE INVENTION

According to the present invention there is provided an organofunctional silicone composition comprising those of the formula: (i) $TD_xM'_3$; (ii) $TD_xD'_yM'_3$; (iii) $TD'_yM'_3$; (iv) $TD_xD'_yM_3$; (v) $TD'_yM_3$; (vi) $M'D_xD'_yM'$; (vii) $M'D_xM'$; (viii) $MD'_yM$; (ix) $MD_xD'_yM$; (x) $M'D'_yM'$; (xi) $M'Q$; (xii) $(D')_z$; or (xiii) a combination of any of the foregoing; wherein T represents a trifunctional siloxy group of the formula $RSiO_{3/2}$ wherein R represents a saturated or unsaturated monovalent hydrocarbon radical; D represents a difunctional siloxy group of the formula $R_2SiO_{2/2}$ wherein each R is independently defined as above; D' represents a difunctional siloxy group of the formula $RR^1SiO_{2/2}$ wherein each R is independently defined as above, $R^1$ is a carboxyalkyl aminoalkyl group of the formula $(HO_2C)(CH_2)_mN(R^2)(CH_2)_n$ where $R^2$ represents hydrogen or an alkyl group of from 1 to 10 carbon atoms, and m and n each independently vary from 1 to 10; M represents a monofunctional siloxy group of the formula $R_3SiO_{1/2}$ wherein each R is independently defined as above; M' represents a monofunctional siloxy group of the formula $R_2R^1SiO_{1/2}$ wherein each R is independently defined as above and $R^1$ is as above defined; Q represents a quadrifunctional siloxy group of the formula $SiO_{4/2}$; x is greater than 1, y is greater than 1 and z is equal to or greater than 3.

Also according to the present invention there is provided a process for preparing the amino acid functionalized silicones of the present invention comprising the steps of: (a) hydrosilating a silicone hydride compound with a lactam to form an amide functionalized silicone; and (b) hydrolyzing the amide functionalized silicone of step (a) to produce an amino acid functionalized silicone.

DETAILED DESCRIPTION OF THE PRESENT INVENTION

The novel amino acid functionalized silicones of the present invention are generally prepared by hydrosilating the appropriate linear, branched or cyclic silicone hydride with a lactam and then hydrolyzing the lactam functionalized silicone to produce the amino acid functionalized silicones of the present invention.

The silicone hydrides for use in the practice of the present invention are typically those which correspond to the product amino acid functionalized siloxanes, and are generally selected from $TD_xM''_3$; $TD_xD''_yM''_3$; $TD''_yM''_3$; $TD_xD''_yM_3$; $TD''_yM_3$; $M''D_xD''_yM''$; $M''D_xM''$; $MD''_yM$; $MD_xD''_yM$; $M''D''_yM''$; $M''Q$; $(D'')_z$; or combinations of any of the foregoing where M'' is a monofunctional siloxy hydride of the formula $(R)_2(H)SiO_{1/2}$; D'' is a difunctional siloxy hydride of the formula $(R)(H)SiO_{2/2}$ and T, D, M, Q, R, x, y, and z are as defined hereinabove. The siloxy hydrides are available commercially and can be prepared by methods known to those skilled in the art.

The lactams useful in the present invention for the hydrosilation reaction are generally of the formula

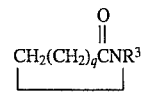

wherein $R^3$ is an alkenyl group of from 2 to about 10 carbon atoms and q is an integer ranging from 1 to about 10. A preferred lactam for use in the practice of the present invention is n-vinyl pyrrolidone, wherein $R^3$ is vinyl, and q is 2 in the above formula.

The lactam is generally reacted with the appropriate silicone hydride by hydrosilation techniques well known to those of ordinary skill in the art. In general the hydrosilation reaction proceeds in the presence of a Group VIII precious metal complex, i.e. platinum, rhodium and/or ruthenium complexes. Such catalyst complexes are well described in the patent literature, e.g., Karstedt, U.S. Pat. No. 3,775,452; Ashby et al., U.S. Pat. No. 4,288,345; Bailey et al., U.S. Pat. No. 3,336,239; Ashby, U.S. Pat. No. 4,421,903; Lamoreaux, U.S. Pat. No. 3,220,972; and Lewis, U.S. Pat. No. 4,946,818. See also, J. Organometallic Chem. 408 (1991) pp. 297–304. A preferred catalyst for use in the present invention comprises tris(dibutylsulfide) rhodium trichloride.

The lactam modified siloxanes are then reacted in a hydrolysis reaction according to techniques known to those skilled in the art. Typically, the hydrolysis reaction is conducted in the presence of an acid, such as dilute sulfuric acid. However, other acids may be employed. The hydrolysis reaction acts to open the amine ring structure to give the corresponding acid. The product is an amino acid functionalized siloxane.

The organofunctional siloxanes of the present invention may be branched (T or Q), linear (D) or cyclic ([D]$_z$). They are of the general formulae: (i) TD$_x$M'$_3$; (ii) TD$_x$D'$_y$M'$_3$; (iii) TD'$_y$M'$_3$; (iv) TD$_x$D'$_y$M$_3$; (v) TD'$_y$M$_3$; (vi) M'D$_x$D'$_y$M'; (vii) M'D$_x$M'; (viii) MD'$_y$M; (ix) MD$_x$D'$_y$M; (x) M'D'$_y$M'; (xi) M'Q; (xii) (D')$_z$; or (xiii) a combination of any of the foregoing. In preferred embodiments, x and y are each independently greater than about 1, preferably each independently ranges from about 1 to about 1000, and more preferably each ranges from about 1 to about 100. In the case of cyclics, z is typically equal to or greater than about 3 and preferably varies from about 4 to about 12.

In the above formulae, each R independently represents a saturated or unsaturated monovalent hydrocarbon, typically containing no more than six carbon atoms and selected from those such as alkyl radicals, e.g., methyl, ethyl and isopropyl; cycloaliphatic radicals, e.g., cyclopentyl and cyclohexenyl; olefinic radicals, e.g., vinyl and allyl; and the phenyl radical.

R$^1$ represents a carboxyalkyl aminoalkyl group of the formula (HO$_2$C)(CH$_2$)$_m$N(R$^2$)(CH$_2$)$_n$ where R$^2$ represents hydrogen or an alkyl group of from 1 to 10 carbon atoms, and m and n each independently vary from 1 to 10. In preferred embodiments, R$^1$ is selected from N-(3-carboxypropyl)-aminoethyl; N-(3-carboxybutyl)aminoethyl; N-(3-carboxymethyl)aminopentyl and the like. Particularly useful in the practice of the present invention is N-(3-carboxypropyl)aminoethyl.

The following reaction scheme depicts the general reaction route for linear materials reacted with n-vinyl pyrrolidone.

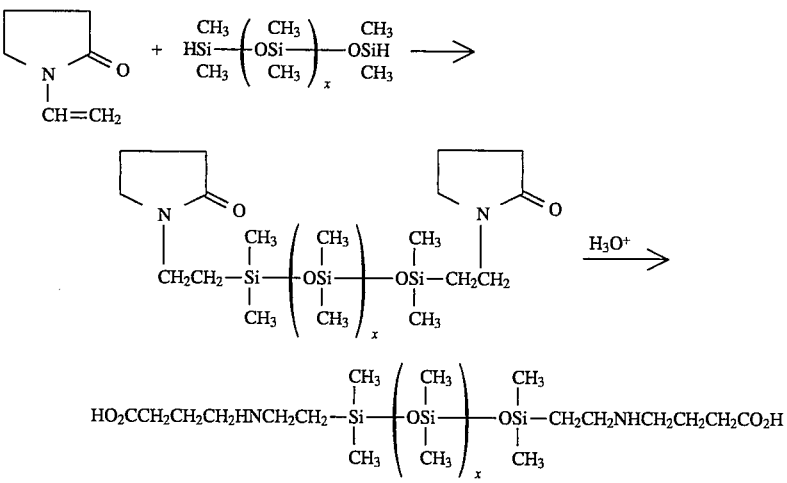

The amino acid functionalized siloxanes of the present invention have uses in a wide variety of personal care and plastics applications, including but not limited to use as plastic additives, hydraulic fluids, vibration damping, release agents. antifoamers, dielectric media, water repellents, surfactants, greases, coagulants, cosmetic and health product additives, heat transfer media, polishes, lubricants, etc.

DESCRIPTION OF THE PREFERRED EMBODIMENTS

The following examples illustrate the present invention. They are not to be construed to limit the scope of the appended claims in any manner whatsoever.

EXAMPLE 1

25.8 g of n-vinyl pyrrolidone and 119 g of toluene were azeotroped for 1.5 hours. The temperature was cooled to 100° C. and one drop of tris(dibutylsulfide) rhodium trichloride catalyst was added. 106.1 g of a branched siloxane of the general formula TD$_{15}$M$^H_3$ where M$^H$ represents a dimethyl hydride siloxane of the formula (CH$_3$)$_2$HSiO$_{1/2}$ is then slowly added. After the addition, the reaction was maintained at reflux. After one hour, an infrared spectrum indicated that the hydride was still present. Two more drops of the catalyst were then added until the hydride band had disappeared. The infrared spectroscopy of this solution indicated that the alkene had disappeared and that the carbonyl had shifted to 1684 cm$^{-1}$.

Five grams of a dilute sulfuric acid solution were then added to the mixture. While refluxing, a black solid deposited on the glass surface. After 2.5 hours, another 20 g of water was added and the entire mixture was allowed to stir for one more hour. The liquids were removed under vacuum to afford an amino acid functional siloxane oil of the present invention which had a broad carbonyl band between 1736 cm$^{-1}$ and 1619 cm$^{-1}$.

EXAMPLE 2

49.2 g of M$^H$M$^H$ siloxane and 189 g of toluene were azeotroped. Three drops of the tris(dibutylsulfide) rhodium trichloride catalyst were then added followed by the slow addition of 81.4 g of n-vinyl pyrrolidone. The mixture was allowed to stir for 3 hours at 100° C. whereupon 10 more drops of the catalyst were added due to indication that the reaction had not proceeded. Within an hour, infrared spectroscopy indicated the reaction was complete. A small portion of this solution was removed, filtered through celite and rotoevaporated using a vacuum pump to isolate the n-vinyl pyrrolidone adduct. 32.5 g of oil was isolated. IR 1684 cm$^{-1}$; NMR CDCl$_3$ standard: 0.05 ppm s,s 12H (Me—Si), 1.09 m 4H (CH$_2$—Si), 2.00 m 4H (CH$_2$), 2.25 m 4H (CH$_2$), 3.27 m 4H (CH$_2$—N), 3.41 m 4H (CH$_2$—N). The NMR assignments are based on the alpha-alpha adduct and comparison of spectra of various substituted pyrrolidones. See, Bovey, F. A., "NMR Data Tables for Organic Compounds" Interscience Publishers, 1967, V. 1.

To the remainder of the mixture, was added 40 ml of water which contained 4 drops of sulfuric acid. The mixture was heated at 90° C. for one hour and then allowed to cool. The mixture was then extracted with toluene, the organic layer subsequently being dried over sodium sulfate and rotoevaporated to afford 67 g of an amino acid functionalized siloxane oil of the present invention. IR 1678 cm$^{-1}$ broad. NMR CDCl$_3$ standard: 0.00 ppm s,s 12H (CH$_3$—Si); 1.02 m 4H (CH$_2$—Si), 1.82 m 4H, 2.19 m 4H, 3.25 m 4H and 3.36 m 4H.

The above-mentioned patents and publications are all hereby incorporated by reference.

Many variations of the present invention will suggest themselves to those skilled in the art in light of the above-detailed description. Other siloxanes may be employed in the present invention, including TD$_x$D'$_y$M'$_3$, TD'$_y$M'$_3$, TD$_x$D'$_y$M$_3$, TD'$_y$M$_3$, M'D$_x$M', MD'$_y$M, MD$_x$D'$_y$M, M'D'$_y$M', M'Q and (D')$_z$ may all be employed in the present invention. Further, a wide variety of lactams other than n-vinyl pyrrolidone are contemplated for use in the present invention. All such obvious modifications are within the full intended scope of the appended claims.

We claim:

1. A method of preparing an organofunctional silicone composition comprising units of the formula
   (i) TD$_x$M'$_3$;
   (ii) TD$_x$D'$_y$M'$_3$;
   (iii) TD'$_y$M'$_3$;
   (iv) TD$_x$D'$_y$M$_3$;
   (v) TD'$_y$M'$_3$;
   (vi) M'D$_x$D'$_y$M';
   (vii) M'D$_x$M';
   (viii) MD'$_y$M;
   (ix) MD$_x$D'$_y$M;
   (x) M'D'$_y$M';
   (xi) M'Q;
   (xii) (D')$_z$; or
   (xiii) a combination of any of the foregoing wherein T represents a trifunctional siloxy group of the formula RSiO$_{3/2}$ wherein R represents independently a saturated or unsaturated monovalent hydrocarbon radical; D represents a difunctional siloxy group of the formula R$_2$SiO$_{2/2}$ wherein each R is independently defined as above; D' represents a difunctional siloxy group of the formula RR$^1$SiO$_{2/2}$ wherein each R is independently defined as above, R$^1$ represents a carboxyalkyl aminoalkyl group of the formula (HO$_2$C)(CH$_2$)$_m$N(R$^2$)(CH$_2$)$_n$ where R$^2$ represents hydrogen or an alkyl group of from 1 to about 10 carbon atoms, and m and n each independently vary from 1 to about 10; M represents a monofunctional siloxy group of the formula R$_3$SiO$_{1/2}$ wherein each R is independently defined as above; M' represents a monofunctional siloxy group of the formula R$_2$R$^1$SiO$_{1/2}$ wherein each R is independently defined as above and R$^1$ is as above defined; Q represents a quadrifunctional siloxy of the formula SiO$_{4/2}$; x is greater than 1, y is greater than 1 and z is equal to or greater than 3;

comprising the steps of:
   (a) hydrosilating a silicone hydride compound with a lactam to form an amide functionalized silicone; and
   (b) hydrolyzing the amide functionalized silicone of step (a) in the presence of an acid catalyst to produce an amino acid functionalized silicone.

2. A process as defined in claim 1 wherein said silicone hydride is selected from TD$_x$M"$_3$; TD$_x$D'$_y$M"$_3$; TD"$_y$M"$_3$; TD$_x$D"$_y$M$_3$; TD"$_y$M$_3$; M"D$_x$D"$_y$M"; M"D$_x$M"; MD"$_y$M; MD$_x$D'$_y$M; M"D"$_y$M"; M"Q; (D")$_z$; or combinations of any of the foregoing where M" is a monofunctional siloxy hydride of the formula (R)$_2$(H)SiO$_{1/2}$; D" is a difunctional siloxy hydride of the formula (R)(H)SiO$_{2/2}$ and T, D, M, Q, R, x, y, and z are as defined above.

3. A process as defined in claim 1 wherein said lactam has the general formula

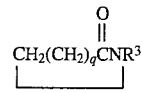

wherein R$^3$ is an alkenyl group of from 2 to 10 carbon atoms and q is an integer ranging from 1 to about 10.

4. A process as defined in claim 3 wherein R is a vinyl group, a is 2 and the lactam is n-vinyl pyrrolidone.

5. A process as defined in claim 1 wherein the hydrosilating step (a) is carried out with a catalyst selected from a rhodium catalyst or a platinum catalyst.

6. A process as defined in claim 1 wherein the hydrolyzing step (b) is carried out with a dilute sulfuric acid.

7. An organofunctional silicone composition prepared by the process as defined in claim 1.

* * * * *